United States Patent [19]
Emery et al.

[11] Patent Number: 5,885,800
[45] Date of Patent: Mar. 23, 1999

[54] DNA ENCODING TUMOR NECROSIS RELATED RECEPTOR, TR4

[75] Inventors: John Emery, Wynnewood; KB Tan, Philadelphia; Alemseged Truneh, West Chester, all of Pa.; Peter R. Young, Lawrenceville, N.J.

[73] Assignee: Smithkline Beecham Corporation, Philadelphia, Pa.

[21] Appl. No.: 794,796

[22] Filed: Feb. 4, 1997

[51] Int. Cl.⁶ .............................. C12N 1/00; C12N 15/00
[52] U.S. Cl. .................... 435/69.1; 435/69.5; 435/252.3; 435/320.1; 536/23.5
[58] Field of Search .................. 435/69.1, 320.1, 435/252.3; 530/350; 536/23.5, 23.8

[56] References Cited

FOREIGN PATENT DOCUMENTS

WO9533051  12/1995   WIPO .
WO9628546   9/1996   WIPO .

OTHER PUBLICATIONS

Accession No. AA577603, Sep. 11, 1997, "National Cancer Institute, Cancer Genome Anatomy Project (CGAP), Tumor Gene Index".
Accession No. AA155646, Jan. 18, 1997, "Wash U–NCI human EST Project".
Ascension No. M91489, Oct. 29,1992, Gieser et al., "Expressed sequence tags and chromosomal localization of cDNA clones from a subtracted retinal pigment epithelium library".
Acension No. W67560, Oct. 16, 1996, Hillier et al., The WashU–Merck EST Project.
Acension No. AA025672, Feb. 1, 1997, Hillier et al., "The WashU–Merck EST Project".
Acension No. AA025673, Feb. 01, 1997, Hillier et al., "The WashU–Merck EST Project".
Lewis et al., "Cloning and expression of cDNAs for two distinct murine tumor necrosis factor receptors demonstrate one receptor is species specific", *Proc. Natl. Acad., Sci, USA*, 88, pp. 2830–2834, (1991).
Goodwin et al., "Molecular Cloning and Expression of the Type 1 and Type 2 Murine Receptors for Tumor Necrosis Factor", *Molecular and Cellular Biology*, 11(6), pp. 3020–3026, (1991).
Smith et al., "A Receptor for Tumor Necrosis Factor Defines an Unusual Family of Cellular and Viral Proteins", *Science*, 248, pp. 1019–1023, (1990).
Powell et al., "Allelic variation of the type 2 tumor necrosis factor receptor gene", *Mammalian Genome*, 5, pp. 726–727, (1994).
Baens et al., "Construction and Evaluation of hncDNA Library of Human 12p. Transcribed Sequences Derived from a Somatic Cell Hydrid", *Genomics*, 16, pp. 214–218, (1993).
Schall, et al. Cell vol. 61: pp. 361–370, Apr. 20, 1990.
Smith, et al. Science vol. 248: pp. 1019–1023, May 24,1990.
Lewis, et al. Proc. Natl. Acad. Sci. USA vol. 88: pp. 2830–2834, Apr. 1991.

*Primary Examiner*—Garnette D. Draper
*Attorney, Agent, or Firm*—William T. Han; William T. King

[57] ABSTRACT

TR4 polypeptides and polynucleotides and methods for producing such polypeptides by recombinant techniques are disclosed. Also disclosed are methods for utilizing TR4 polypeptides and polynucleotides in the design of protocols for the treatment of chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atheroschlerosis, and Alzheimers disease among others, and diagnostic assays for such conditions.

16 Claims, 3 Drawing Sheets

Nucleotide and Amino Acid sequence of TR4 (SEQ ID NOS: 1 and 2, respectively.)

SEQ ID No. 1

```
                10                    30                    50
                 .                     .                     .
      CCCACGCGTCCGCCCACGCGTCCGCCCACGCGTCCGGGTGGCATGTCGGTCAGGCACAGC 70                    90                   110
                 .                     .                     .
      AGGGTCCTGTGTCCGCGCTGAGCCGCGCTCTCCCTGCTCCAGCAAGGACCATGAGGGCGC
                                                           MetArgAlaL 130                   150                   170
                 .                     .                     .
      TGGAGGGGCCAGGCCTGTCGCTGCTGTGCCTGGTGTTGGCGCTGCCTGCCCTGCTGCCGG
      euGluGlyProGlyLeuSerLeuLeuCysLeuValLeuAlaLeuProAlaLeuLeuProV 190                   210                   230
                 .                     .                     .
      TGCCGGCTGTACGCGGAGTGGCAGAAACACCCACCTACCCCTGGCGGGACGCAGAGACAG
      alProAlaValArgGlyValAlaGluThrProThrTyrProTrpArgAspAlaGluThrG 250                   270                   290
                 .                     .                     .
      GGGAGCGGCTGGTGTGCGCCCAGTGCCCCCCAGGCACCTTTGTGCAGCGGCCGTGCCGCC
      lyGluArgLeuValCysAlaGlnCysProProGlyThrPheValGlnArgProCysArgA 310                   330                   350
                 .                     .                     .
      GAGACAGCCCCACGACGTGTGGCCCGTGTCCACCGCGCCACTACACGCAGTTCTGGAACT
      rgAspSerProThrThrCysGlyProCysProProArgHisTyrThrGlnPheTrpAsnT 370                   390                   410
                 .                     .                     .
      ACCTGGAGCGCTGCCGCTACTGCAACGTCCTCTGCGGGGAGCGTGAGGAGGAGGCACGGG
      yrLeuGluArgCysArgTyrCysAsnValLeuCysGlyGluArgGluGluGluAlaArgA 430                   450                   470
```

FIG. 1

```
CTTGCCACGCCACCCACAACCGTGCCTGCCGCTGCCGCACCGGCTTCTTCGCGCACGCTG
 laCysHisAlaThrHisAsnArgAlaCysArgCysArgThrGlyPhePheAlaHisAlaG
```
         490                510                530

```
GTTTCTGCTTGGAGCACGCATCGTGTCCACCTGGTGCCGGCGTGATTGCCCCGGGCACCC
 lyPheCysLeuGluHisAlaSerCysProProGlyAlaGlyValIleAlaProGlyThrP
```
         550                570                590

```
CCAGCCAGAACACGCAGTGCCAGCCGTGCCCCCCAGGCACCTTCTCAGCCAGCAGCTCCA
 roSerGlnAsnThrGlnCysGlnProCysProProGlyThrPheSerAlaSerSerSerS
```
         610                630                650

```
GCTCAGAGCAGTGCCAGCCCCACCGCAACTGCACGGCCCTGGGCCTGGCCCTCAATGTGC
 erSerGluGlnCysGlnProHisArgAsnCysThrAlaLeuGlyLeuAlaLeuAsnValP
```
         670                690                710

```
CAGGCTCTTCCTCCCATGACACCCTGTGCACCAGCTGCACTGGCTTCCCCCTCAGCACCA
 roGlySerSerSerHisAspThrLeuCysThrSerCysThrGlyPheProLeuSerThrA
```
         730                750                770

```
GGGTACCAGGAGCTGAGGAGTGTGAGCGTGCCGTCATCGACTTTGTGGCTTTCCAGGACA
 rgValProGlyAlaGluGluCysGluArgAlaValIleAspPheValAlaPheGlnAspI
```
         790                810                830

```
TCTCCATCAAGAGGCTGCAGCGGCTGCTGCAGGCCCTCGAGGCCCCGGAGGGCTGGGGTC
 leSerIleLysArgLeuGlnArgLeuLeuGlnAlaLeuGluAlaProGluGlyTrpGlyP
```
         850                870                890

```
CGACACCAAGGGCGGGCCGCGCGGCCTTGCAGCTGAAGCTGCGTCGGCGGCTCACGGAGC
 roThrProArgAlaGlyArgAlaAlaLeuGlnLeuLysLeuArgArgArgLeuThrGluL
```
         910                930                950

FIG. 1A

TCCTGGGGGCGCAGGACGGGGCGCTGCTGGTGCGGCTGCTGCAGGCGCTGCGCGTGGCCA
euLeuGlyAlaGlnAspGlyAlaLeuLeuValArgLeuLeuGlnAlaLeuArgValAlaA 970                 990                1010

GGATGCCCGGGCTGGAGCGGAGCGTCCGTGAGCGCTTCCTCCCTGTGCACTGATCCTGGC
rgMetProGlyLeuGluArgSerValArgGluArgPheLeuProValHisEnd 1030                1050                1070

CCCCTCTTATTTATTCTACATCCTTGGCACCCCACTTGCACTGAAAGAGGCTTTTTTTTA 1090                1110                1130

AATAGAAGAAATGAGGTTTCTTAAAGCTTATTTTTATAAAGCTTTTTCATAAAAAAAAAA

1150

AAAAAAAAAAAAAAAAAAAAAAAA

DNA ENCODING TUMOR NECROSIS RELATED RECEPTOR, TR4

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Tumor necrosis factor receptor (TNF-R) family, hereinafter referred to as TR4. The invention also relates to inhibiting or activating the action of such polynucleotides and polypeptides.

BACKGROUND OF THE INVENTION

Many biological actions, for instance, response to certain stimuli and natural biological processes, are controlled by factors, such as cytokines. Many cytokines act through receptors by engaging the receptor and producing an intracellular response.

For example, tumor necrosis factors (TNF) alpha and beta are cytokines which act through TNF receptors to regulate numerous biological processes, including protection against infection and induction of shock and inflammatory disease. The TNF molecules belong to the "TNF-ligand" superfamily, and act together with their receptors or counterligands, the "TNF-receptor" superfamily. So far, nine members of the TNF ligand superfamily have been identified and ten members of the TNF-receptor superfamily have been characterized.

Among the ligands there are included TNF-a, lymphotoxin-a (LT-a, also known as TNF-b), LT-b (found in complex heterotrimer LT-a2-b), FasL, CD40L, CD27L, CD30L, 4-1BBL, OX40L and nerve growth factor (NGF)). The superfamily of TNF receptors includes the p55TNF receptor, p75TNF receptor, TNF receptor-related protein, FAS antigen or APO-1, CD40, CD27, CD30, 4-1BB, OX40, low affinity p75 and NGF-receptor (Meager, A., Biologicals, 22:291–295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga, R., et al., Nature 356:314 (1992)), perhaps reflecting a failure of programmed cell death. Mutations of the CD40 ligand cause an X-linked immunodeficiency state characterized by high levels of immunoglubulin M and low levels of immunoglobulin G in plasma, indicating faulty T-cell-dependent B-cell activation (Allen, R. C. et al., Science 259:990 (1993)). Targeted mutations of the low affinity nerve growth factor receptor cause a disorder characterized by faulty sensory innovation of peripheral structures (Lee, K. F. et al, Cell 69:737 (1992)).

TNF and LT-a are capable of binding to two TNF receptors (the 55- and 75-kd TNF receptors). A large number of biological effects elicited by TNF and LT-a, acting through their receptors, include hemorrhagic necrosis of transplanted tumors, cytotoxicity, a role in endotoxic shock, inflammation, immunoregulation, proliferation and antiviral responses, as well as protection against the deleterious effects of ionizing radiation. TNF and LT-a are involved in the pathogenesis of a wide range of diseases, including endotoxic shock, cerebral malaria, tumors, autoimmuine disease, AIDS and graft-host rejection (Beutler, B. and Von Huffel, C., Science 264:667–668 (1994)). Mutations in the p55 Receptor cause increased susceptibility to microbial infection.

Moreover, an about 80 amino acid domain near the C-terminus of TNFR1 (P55) and Fas was reported as the "death domain," which is responsible for transducing signals for programmed cell death (Tartaglia et al., Cell 74:845 (1993)).

The effects of TNF family ligands and TNF family receptors are varied and influence numerous functions, both normal and abnormal, in the biological processes of the mammalian system. There is a clear need, therefore, for identification and characterization of such receptors and ligands that influence biological activity, both normally and in disease states. In particular, there is a need to isolate and characterize novel members of the TNF receptor family.

This indicates that these Tumor necrosis factor receptors (TNF-R) have an established, proven history as therapeutic targets. Clearly there is a need for identification and characterization of further members of Tumor necrosis factor receptor (TNF-R) family which can play a role in preventing, ameliorating or correcting dysfunctions or diseases, including, but not limited to, chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atheroschlerosis, and Alzheimers disease.

SUMMARY OF THE INVENTION

In one aspect, the invention relates to TR4 polypeptides and recombinant materials and methods for their production. Another aspect of the invention relates to methods for using such TR4 polypeptides and polynucleotides. Such uses include the treatment of chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atheroschlerosis, and Alzheimers disease, among others. In still another aspect, the invention relates to methods to identify agonists and antagonists using the materials provided by the invention, and treating conditions associated with TR4 imbalance with the identified compounds. Yet another aspect of the invention relates to diagnostic assays for detecting diseases associated with inappropriate TR4 activity or levels.

BRIEF DESCRIPTION OF THE DRAWINGS

FIG. 1 shows the nucleotide and deduced amino acid sequence of human TR4. SEQ ID NOS: 1 and 2.

DESCRIPTION OF THE INVENTION

Definitions

The following definitions are provided to facilitate understanding of certain terms used frequently herein.

"TR4" refers generally to a polypeptide having the amino acid sequence set forth in SEQ ID NO:2 or an allelic variant thereof.

"TR4 activity or TR4 polypeptide activity" or "biological activity of the TR4 or TR4 polypeptide" refers to the metabolic or physiologic function of said TR4 including similar activities or improved activities or these activities with decreased undesirable side-effects. Also included are antigenic and immunogenic activities of said TR4.

"TR4 polypeptides" refers to polypeptides with amino acid sequences sufficiently similar to TR4 sequences, preferably exhibiting at least one biological activity of the TR4.

"TR4 gene" refers to a polynucleotide having the nucleotide sequence set forth in SEQ ID NO:1 or allelic variants thereof and/or their complements.

"TR4 polynucleotides" refers to polynucleotides containing a nucleotide sequence which encodes a TR4 polypeptide or fragment thereof, or a nucleotide sequence which has at least 58% identity to a nucleotide sequence encoding the polypeptide of SEQ ID NO:2 or the corresponding fragment thereof, or a nucleotide sequence which has sufficient identity to a nucleotide sequence contained in SEQ ID NO:1 to hybridize under conditions useable for amplification or for use as a probe or marker.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al, "Protein Synthesis: Posttranslational Modifications and Aging", *Ann N.Y. Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., SIAM J Applied Math (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., SIAM J Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al, J Molec Biol (1990) 215:403).

Polypeptides of the Invention

The TR4 polypeptides of the present invention include the polypeptide of SEQ ID NO:2 (in particular the mature polypeptide) as well as TR4 polypeptides and which have at least 80% identity to the polypeptide of SEQ ID NO:2 or the relevant portion and more preferably at least 85% identity, and still more preferably at least 90% identity, and even still more preferably at least 95% identity to SEQ ID NO: 2.

The TR4 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the TR4 polypeptides are also included in the invention. A fragment is a polypeptide having an amino acid sequence that entirely is the same as part, but not all, of the amino acid sequence of the aforementioned TR4 polypeptides. As with TR4 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of TR4 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of TR4 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterize by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate TR4 activity, including those with a similar activity or an improved activity, or with a decreased undesirable activity. Also included are those that are antigenic or immunogenic in an animal, especially in a human.

Thus, the polypeptides of the invention include polypeptides having an amino acid sequence at least 80% identical to that of SEQ ID NO:2 or fragments thereof with at least 80% identity to the corresponding fragment of SEQ ID NO:2. Preferably, all of these polypeptides retain the biological activity of the TR4, including antigenic activity. Included in this group are variants of the defined sequence and fragments. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The TR4 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to isolated polynucleotides which encode the TR4 polypeptides and polynucleotides closely related thereto.

TR4 of the invention is structurally related to other proteins of the Tumor necrosis factor receptor (TNF-R), as shown by the results of sequencing the cDNA encoding human TR4. The cDNA sequence contains an open reading frame encoding a protein of 300 with a deduced molecular weight of 32.7 kDa. TR4 of FIG. 1 (SEQ ID NO:2) has about 29.5% identity (using BESTFIT (from GCG suite of Programs)) in 294 amino acid residues with Murine tumor necrosis factor receptor 2 (TNF-R2) (M. Lewis et al., Proc Natl. Acad. Sci. USA. 88:2830–2834(1991); R. G. Goodwin et al., Mol Cell. Biol.11:3020–3026(1991)). Furthermore, TR4 (SEQ ID NO:2) is 29.4% identical to human TNF-R2 over 300 amino acid residues (C. A. Smith et al., Science 248:1019–1023(1990)). TR4 gene of FIG. 1 (SEQ ID NO:1) has about 58% identity (using BLAST) in 120 nucleotide residues with Humnan Tumor necrosis factor receptor 2 related protein mRNA (M. Baens et al., Genomics 16, 214–218 (1993)). Furthermore, TR4 is 58% identical to murine TNF-R2 mRNA over 148 nucleotide base residues (E. E. Powell et al., Mamm. Genome 5, 726–727 (1994)).

One polynucleotide of the present invention encoding TR4 may be obtained using standard cloning and screening, from a cDNA library derived from mRNA in cells of human keratinocytes, pancreatic tumor, lung endothelium, prostate, cerebellum, fetal heart, retinal pigment epithelium, progesterone treated endometrial stromal cells using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

Thus, the nucleotide sequence encoding TR4 polypeptides may be identical over its entire length to the coding sequence in FIG. 1 (SEQ ID NO:1), or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention contain a nucleotide sequence that is highly identical, at least 80% identical, with a nucleotide sequence encoding a TR4 polypeptide, or at least 80% identical with the encoding nucleotide sequence set forth in FIG. 1 (SEQ ID NO:1), or at least 80% identical to a nucleotide sequence encoding the polypeptide of SEQ ID NO:2.

When the polynucleotides of the invention are used for the recombinant production of TR4 polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or preproprotein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosorne binding sites and sequences that stabilize mRNA.

Among particularly preferred embodiments of the invention are polynucleotides encoding TR4 polypeptides having the amino acid sequence of set out in FIG. 1 (SEQ ID NO:2) and variants thereof.

Further preferred embodiments are polynucleotides encoding TR4 variants that have the amino acid sequence of the TR4 polypeptide of FIG. 1 (SEQ ID NO:2) in which several, 5–10, 1–5, 1–3, 1–2 or 1 amino acid residues are substituted, deleted or added, in any combination.

Further preferred embodiments of the invention are polynucleotides that are at least 80% identical over their entire length to a polynucleotide encoding the TR4 polypeptide having the amino acid sequence set out in FIG. 1 (SEQ ID NO:2), and polynucleotides which are complementary to such polynucleotides. In this regard, polynucleotides at least 80% identical over their entire length to the same are particularly preferred, and those with at least 90% are especially preferred. Furthermore, those with at least 97% are highly preferred and those with at least 98–99% are most highly preferred, with at least 99% being the most preferred.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are sufficiently identical to a nucleotide sequence contained in SEQ ID NO:1, may be used as hybridization probes for cDNA and genomic DNA, to isolate full-length cDNAs and genomic clones encoding TR4 polypeptide and to isolate cDNA and genomic clones of other genes that have a high sequence similarity to the TR4 gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animnal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al, *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the TR4 polypeptide is to be expressed for use in screening assays, the polypeptide may be produced at the surface of the cell. In this event, the cells may be harvested prior to use in the screening assay. If TR4 polypeptide is secreted into the medium, the medium can be recovered in order to recover and purify the polypeptide; if produced intracellularly, the cells must first be lysed before the polypeptide is recovered.

TR4 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of TR4 polynucleotides for use as diagnostic reagents. Detection of a mutated form of TR4 gene associated with a dysfunction will provide a diagnostic tool that can add to or define a diagnosis of a disease or susceptibility to a disease which results from under-expression, over-expression or altered expression of TR4. Individuals carrying mutations in the TR4 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled TR4 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al, *Proc Natl Acad Sci USA* (1985) 85:4397–4401. In another embodiment, an array of oligonucleotides probes comprising TR4 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to chronic and acute inflammnation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atheroschlerosis, and Alzheimers disease through detection of mutation in the TR4 gene by the methods described.

In addition, chronic and acute inflammation, arhritis, septicemia, autoimmune diseases (eg inflammatory bowel disease, psoriasis), transplant rejection, graft vs. host disease, infection, stroke, ischernia, acute respiratory disease syndrome, restenosis, brain injury, AIDS, Bone diseases, cancer (eg lymphoproliferative disorders), atheroschlerosis, and Alzheimers disease can be diagnosed by methods comprising determining from a sample derived from a subject an abnormally decreased or increased level of TR4 polypeptide or TR4 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an TR4 polypeptide, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the TR4 polypeptides. The term "immunospecific" means that the antibodies have substantiall greater affinity for the polypeptides of the invention than their affinity for other related polypeptides in the prior art.

Antibodies generated against the TR4 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against TR4 polypeptides may also be employed to treat chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atheroschlerosis, and Alzheimers disease among others.

Vaccines

Another aspect of the invention relates to a method for inducing an immunological response in a mammal which comprises inoculating the mammal with TR4 polypeptide, or a fragment thereof, adequate to produce antibody and/or T cell immune response to protect said animal from chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atheroschlerosis, and Alzheimers disease among others. Yet another aspect of the invention relates to a method of inducing immunological response in a mammal which comprises, delivering TR4 gene via a vector directing expression of TR4 polypeptide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a TR4 polypeptide wherein the composition comprises a TR4 polypeptide or TR4 gene. The vaccine formulation may further comprise a suitable carrier. Since TR4 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The TR4 polypeptide of the present invention may be employed in a screening process for compounds which activate (agonists) or inhibit activation of (antagonists, or otherwise called inhibitors) the TR4 polypeptide of the present invention. Thus, polypeptides of the invention may also be used to assess identify agonist or antagonists from, for example, cells, cell-free preparations, chemical libraries, and natural product mixtures. These agonists or antagonists may be natural substrates, ligands, receptors, etc., as the case may be, of the polypeptide of the present invention; or may be structural or functional mimetics of the polypeptide of the present invention. See Coligan et al., Current Protocols in Immunology1(2):Chapter 5 (1991).

TR4 proteins are ubiquitous in the mammalian host and are responsible for many biological functions, including many pathologies. Accordingly, it is desirous to find compounds and drugs which stimulate TR4 polypeptide on the one band and which can inhibit the function of TR4 polypeptide on the other hand. In general, agonists are employed for therapeutic and prophylactic purposes for such conditions as chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atheroschlerosis, and Alzheimers disease. Antagonists may be employed for a variety of therapeutic and prophylactic purposes for such conditions as chronic and acute inflammation, arthritis, septicemia, autoimmune diseases (eg inflammatory bowel disease, psoriasis), transplant rejection, graft vs. host disease, infection, stroke, ischemia, acute respiratory disease syndrome, restenosis, brain injury, AIDS, Bone diseases, cancer (eg lymphoproliferative disorders), atheroschlerosis, and Alzheimers disease.

Such screening procedures may involve producing appropriate cells which express the TR4 polypeptide of the present invention on the surface thereof. Such cells include cells from mammals, yeast, Drosophila or E. coli. Cells expressing the TR4 polypeptide (or cell membrane containing the expressed polypeptide) fused to the membrane and intracellular domains of any single transmembrane receptor, prefereably one with a known functional readout upon ligand binding (eg as tyrosine kinase domain) are then contacted with a test compound to observe binding, or stimulation or inhibition of a functional response.

The assays may simply test binding of a candidate compound wherein adherence to the cells bearing the TR4 polypeptide is detected by means of a label directly or indirectly associated with the candidate compound or in an assay involving competition with a labeled competitor. Further, these assays may test whether the candidate compound results in a signal generated by activation of the TR4 polypeptide, using detection systems appropriate to the cells bearing the TR4 polypeptide at their surfaces. Inhibitors of activation are generally assayed in the presence of a known agonist and the effect on activation by the agonist by the presence of the candidate compound is observed. Standard methods for conducting such screening assays are well understood in the art.

Alternatively, TR4 may be expressed as a soluble protein, including versions which fuse all or part of TR4 with a convenient partner peptide for which detection reagents are available, eg TR4-IgG fusions, and used in a solid state or solution phase binding assay. For example, the soluble TR4 can be used to detect agonist or antagonist binding directly through changes that can be detected experimentally, eg surface plasmon resonance, nuclear magnetic resonance spectrometry, sedimentation, calorimetry. The soluble TR4 can be used to detect agonist or antagonist binding indirectly by looking for competition of the candidate agonist or antagonist with a ligand whose binding can be detected. Ligand detection methods include antibody recognition, modification of the ligand via radioactive labeling, chemical modification (eg biotinylation), fusion to an epitope tag. Methods include ELISA based assays, immunoprecipitation and scintillation proximity.

Assays similar to those described above using soluble or membrane bound TR4 may also be used to identify and purify the natural ligand(s) of TR4. These ligands may be agonists or antagonists of the receptor.

Examples of potential TR4 polypeptide antagonists include antibodies or, in some cases, oligonucleotides or proteins which are closely related to the ligands, substrates, receptors, etc., as the case may be, of the TR4 polypeptide, e.g., a fragment of the ligands, substrates, receptors, or small molecules which bind to the polypeptide of the present invention but do not elicit a response, so that the activity of the polypeptide is prevented.

The TR4 cDNA, protein and antibodies to the protein may also be used to configure assays for detetcting the effect of added compounds on the production of TR4 mRNA and protein in cells. For example, an ELISA may be constructed for measuring secreted or cell associated levels of TR4 protein using monoclonal and polyclonal antibodies by standard methods known in the art, and this can be used to discover agents (i.e. antagonists or agonists) which may inhibit or enhance the production of TR4 from suitably manipulated cells or tissues.

Prophylactic and Therapeutic Methods

This invention provides methods of treating an abnormal conditions related to both an excess of and insufficient amounts of TR4 polypeptide activity.

If the activity of TR4 polypeptide is in excess, several approaches are available. One approach comprises administering to a subject an inhibitor compound (antagonist) as hereinabove described along with a pharmaceutically acceptable carrier in an amount effective to inhibit activation by blocking binding of ligands to the TR4 polypeptide, or by inhibiting a second signal, and thereby alleviating the abnormal condition.

In another approach, soluble forms of TR4 polypeptides still capable of binding the ligand in competition with endogenous TR4 polypeptide may be administered. Typical embodiments of such competitors comprise fragments of the TR4 polypeptide.

In still another approach, expression of the gene encoding endogenous TR4 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al, *Science* (1988) 241:456; Dervan et al, *Science* (1991) 251:1360. These oligomers can be administered per se or the relevant oligomers can be expressed in vivo.

For treating abnormal conditions related to an underexpression of TR4 and its activity, several approaches are also available. One approach comprises administering to a subject a therapeutically effective amount of a compound which activates TR4 polypeptide, i.e., an agonist as described above, in combination with a pharmaceutically acceptable carrier, to thereby alleviate the abnormal condition. Alternatively, gene therapy may be employed to effect the endogenous production of TR4 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy* and other *Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of TR4 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

An EST (EST#1650779; Project ID HKAAW85) with sequence similarity to the human TNF receptor was discovered in a commercial EST database. A search through several overlapping ESTs allowed the selection of the 5' most EST (EST#1663724; Project ID HKABP82), which was completely sequenced. Analysis of the 1164 nucleotide cDNA sequence indicated that it encoded an open reading frame for a novel member of the TNF receptor superfamily and was named TR4. The predicted protein is 300 amino acids long, and contains an amino-terninal hydrophobic signal sequence required for secretion. Cleavage after amino acid #29. This means that the signal sequence is amino acids 1–29 and the mature protein is amino acids 30–300 (ie 271 residues). Furthermore, the protein does not contain a hydrophobic membrane spanning region suggesting that it is a secreted protein. Comparison of TR4 with other TNF receptor family proteins indicates that it has at least three of the cysteine-rich repeats characteristic of the extracellular domains of this family. There is a fourth more weakly related repeat which nevertheless retained several though not all of the most conserved residues.

Example 2

Northern blot of TR4.

Various tissues and cell lines were screened for mRNA expression by Northern blot. RNA was prepared from cells and cell lines using Tri-Reagent (Molecular Research Center Inc., Cincinnati, Ohio), run in denaturing agarose gels (Sambrook et al., Molecular Cloning: a laboratory manual, 2nd Ed. Cold Spring Harbor Lab Press, N.Y. (1989)) and transfered to Zeta-probe nylon membrane (Biorad, Hercules, Calif.) via vacuum blotting in 25 mM NaOh for 90 min. After neutralization for 5–10 minutes with 1M tris-HCl, pH 7.5 containing 3M NaCl, the blots were prehybridized with 50% formamide, 8% dextran sulfate, 6XSSPE, 0.1% SDS and 100 $\mu$g/ml of sheared and dentured salmon sperm DNA for at least 30 min. At 42° C. cDNA probes were labeled with 32P-CTP by random priming (Statagene, La Jolla, Calif.), briefly denatured with 0.25M NaOH and added to the prehybridization solution. After a further incubation for at least 24 h at 42° C., the blots were washed in high stringency conditions and exposed to X-ray film.

Very high expression of TR4 RNA was detected in spleen. High expression was also detected in lung. Low expression was detected in thymus and heart. Low but detectable levels were also observed in kidney and prostate. Other tissues evaluated include brain, liver, small intestine and skeletal muscle.

TR4 RNA was not expressed in resting or activated lymphocytes, bone marrow or monocytes. TR4 was highly expressed in aortic endothelial cells. RNA was also detected in HTB11 neuroblastoma cell line. Other cell lines examined include KG1a, HL60, U937, THP1 and Jurkat cells.

The major RNA form is 1.5 kb in size. There appears to be a minor form of 3.5 kb in size. The 1.5 kb RNA was not detected in U937 cells but was highly inducible following stimulation with DMSO (which generally leads to granulocytic differentiation) but not PMA (which generally leads to monocytic differentiation).

What is claimed is:

1. An isolated polynucleotide comprising a polynucleotide of SEQ ID NO:1.

2. An isolated polynucleotide comprising a polynucleotide which encodes the polypeptide of SEQ ID NO:2.

3. The isolated polynucleotide of SEQ ID NO:1.

4. The isolated polynucleotide contained in SEQ ID NO:1 which encodes the polypeptide of SEQ ID NO:2.

5. An isolated polynucleotide comprising a nucleotide sequence that has at least 90% identity to a nucleotide sequence contained in SEQ ID NO:1, in which the percent identity is calculated using FASTA wherein the sequences are aligned so that the highest order match is obtained.

6. An isolated polynucleotide comprising a nucleotide sequence that has at least 95% identity to a nucleotide sequence contained in SEQ ID NO:1, in which the percent identity is calculated using FASTA wherein the sequences are aligned so that the highest order match is obtained.

7. An isolated polynucleotide comprising a nucleotide sequence that has at least 90% identity to a nucleotide sequence encoding the polypeptide of SEQ ID NO:2, in which the percent identity is calculated using FASTA wherein the sequences are aligned so that the highest order match is obtained.

8. An isolated polynucleotide comprising a nucleotide sequence that has at least 95% identity to a nucleotide sequence encoding the polypeptide of SEQ ID NO:2, in which the percent identity is calculated using FASTA wherein the sequences are aligned so that the highest order match is obtained.

9. The polynucleotide which is the RNA transcript of SEQ ID NO:1.

10. The isolated polynucleotide which is the RNA transcript of the coding region of the of SEQ ID NO:1.

11. An isolated polynucleotide which is comtplementary to any of the polynucleotides of claims 1, 2, 3, 4, 9 or 10.

12. The isolated polynucleotide of claim 2 which is DNA or RNA.

13. A DNA or RNA molecule comprising an expression vector wherein said expression vector is capable of producing a TR4 polypeptide of SEQ ID NO:2 wherein said expression vector comprises a polynucleotide which encodes the polypeptide of SEQ ID NO.2 and a control region operatively linked to said polynucleotide, when said expression vector is present in a compatible host cell.

14. A host cell comprising the expression vector of claim 13.

15. A process for producing a TR4 polypeptide comprising culturing a host of claim 14 and under conditions sufficient for the production of said polypeptide and recovering said polypeptide from the culture.

16. A process for producing a cell which produces a TR4 polypeptide comprising transforming or transfecting a host cell with the expression vector of claim 13 such that the host cell, under appropriate culture conditions, produces said polypeptide.

* * * * *

Adverse Decisions in Interference

Patent No. 5,885,800, John Emery, Kb Tan, Alem Truneh and Peter Young, DNA ENCODING TUMOR NECROSIS RELATED RECEPTOR,TR4 , Interference No. 105,701, final judgment adverse to the patentees rendered September 14, 2009, as to claims 2, 4-8 & 11-16.

(*Official Gazette, July 27, 2010*)

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1164 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
CCCACGCGTC  CGCCCACGCG  TCCGCCCACG  CGTCCGGGTG  GCATGTCGGT  CAGGCACAGC      60
AGGGTCCTGT  GTCCGCGCTG  AGCCGCGCTC  TCCCTGCTCC  AGCAAGGACC  ATGAGGGCGC     120
TGGAGGGGCC  AGGCCTGTCG  CTGCTGTGCC  TGGTGTTGGC  GCTGCCTGCC  CTGCTGCCGG     180
TGCCGGCTGT  ACGCGGAGTG  GCAGAAACAC  CCACCTACCC  CTGGCGGGAC  GCAGAGACAG     240
GGGAGCGGCT  GGTGTGCGCC  CAGTGCCCCC  CAGGCACCTT  TGTGCAGCGG  CCGTGCCGCC     300
```

| | | | | | |
|---|---|---|---|---|---|
|GAGACAGCCC|CACGACGTGT|GGCCCGTGTC|CACCGCGCCA|CTACACGCAG|TTCTGGAACT|360|
|ACCTGGAGCG|CTGCCGCTAC|TGCAACGTCC|TCTGCGGGGA|GCGTGAGGAG|GAGGCACGGG|420|
|CTTGCCACGC|CACCCACAAC|CGTGCCTGCC|GCTGCCGCAC|CGGCTTCTTC|GCGCACGCTG|480|
|GTTTCTGCTT|GGAGCACGCA|TCGTGTCCAC|CTGGTGCCGG|CGTGATTGCC|CCGGGCACCC|540|
|CCAGCCAGAA|CACGCAGTGC|CAGCCGTGCC|CCCCAGGCAC|CTTCTCAGCC|AGCAGCTCCA|600|
|GCTCAGAGCA|GTGCCAGCCC|CACCGCAACT|GCACGGCCCT|GGGCCTGGCC|CTCAATGTGC|660|
|CAGGCTCTTC|CTCCCATGAC|ACCCTGTGCA|CCAGCTGCAC|TGGCTTCCCC|CTCAGCACCA|720|
|GGGTACCAGG|AGCTGAGGAG|TGTGAGCGTG|CCGTCATCGA|CTTTGTGGCT|TTCCAGGACA|780|
|TCTCCATCAA|GAGGCTGCAG|CGGCTGCTGC|AGGCCCTCGA|GGCCCCGGAG|GGCTGGGGTC|840|
|CGACACCAAG|GGCGGGCCGC|GCGGCCTTGC|AGCTGAAGCT|GCGTCGGCGG|CTCACGGAGC|900|
|TCCTGGGGGC|GCAGGACGGG|GCGCTGCTGG|TGCGGCTGCT|GCAGGCGCTG|CGCGTGGCCA|960|
|GGATGCCCGG|GCTGGAGCGG|AGCGTCCGTG|AGCGCTTCCT|CCCTGTGCAC|TGATCCTGGC|1020|
|CCCCTCTTAT|TTATTCTACA|TCCTTGGCAC|CCCACTTGCA|CTGAAAGAGG|CTTTTTTTA|1080|
|AATAGAAGAA|ATGAGGTTTC|TTAAAGCTTA|TTTTTATAAA|GCTTTTTCAT|AAAAAAAAAA|1140|
|AAAAAAAAAA|AAAAAAAAAA|AAAA| | |1164|

( 2 ) INFORMATION FOR SEQ ID NO:2:

( i ) SEQUENCE CHARACTERISTICS:
        ( A ) LENGTH: 300 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Arg Ala Leu Glu Gly Pro Gly Leu Ser Leu Leu Cys Leu Val Leu
 1               5                  10                  15

Ala Leu Pro Ala Leu Leu Pro Val Pro Ala Val Arg Gly Val Ala Glu
            20                  25                  30

Thr Pro Thr Tyr Pro Trp Arg Asp Ala Glu Thr Gly Glu Arg Leu Val
        35                  40                  45

Cys Ala Gln Cys Pro Pro Gly Thr Phe Val Gln Arg Pro Cys Arg Arg
    50                  55                  60

Asp Ser Pro Thr Thr Cys Gly Pro Cys Pro Arg His Tyr Thr Gln
65                  70                  75                  80

Phe Trp Asn Tyr Leu Glu Arg Cys Arg Tyr Cys Asn Val Leu Cys Gly
                85                  90                  95

Glu Arg Glu Glu Glu Ala Arg Ala Cys His Ala Thr His Asn Arg Ala
               100                 105                 110

Cys Arg Cys Arg Thr Gly Phe Phe Ala His Ala Gly Phe Cys Leu Glu
           115                 120                 125

His Ala Ser Cys Pro Pro Gly Ala Gly Val Ile Ala Pro Gly Thr Pro
       130                 135                 140

Ser Gln Asn Thr Gln Cys Gln Pro Cys Pro Gly Thr Phe Ser Ala
145                 150                 155                 160

Ser Ser Ser Ser Ser Glu Gln Cys Gln Pro His Arg Asn Cys Thr Ala
                165                 170                 175

Leu Gly Leu Ala Leu Asn Val Pro Gly Ser Ser Ser His Asp Thr Leu
               180                 185                 190
```

-continued

| Cys | Thr | Ser 195 | Cys | Thr | Gly | Phe | Pro 200 | Leu | Ser | Thr | Arg | Val 205 | Pro | Gly | Ala |
| --- | --- | --- | --- | --- | --- | --- | --- | --- | --- | --- | --- | --- | --- | --- | --- |
| Glu | Glu 210 | Cys | Glu | Arg | Ala | Val 215 | Ile | Asp | Phe | Val | Ala 220 | Phe | Gln | Asp | Ile |
| Ser 225 | Ile | Lys | Arg | Leu | Gln 230 | Arg | Leu | Leu | Gln | Ala 235 | Leu | Glu | Ala | Pro | Glu 240 |
| Gly | Trp | Gly | Pro | Thr 245 | Pro | Arg | Ala | Gly | Arg 250 | Ala | Ala | Leu | Gln | Leu 255 | Lys |
| Leu | Arg | Arg | Arg 260 | Leu | Thr | Glu | Leu | Leu 265 | Gly | Ala | Gln | Asp | Gly 270 | Ala | Leu |
| Leu | Val | Arg 275 | Leu | Leu | Gln | Ala | Leu 280 | Arg | Val | Ala | Arg | Met 285 | Pro | Gly | Leu |
| Glu | Arg 290 | Ser | Val | Arg | Glu | Arg 295 | Phe | Leu | Pro | Val | His 300 | | | | |